(12) United States Patent
Takahashi et al.

(10) Patent No.: US 9,339,766 B2
(45) Date of Patent: May 17, 2016

(54) METHOD AND APPARATUS FOR PURIFYING ALCOHOL

(75) Inventors: Kazushige Takahashi, Tokyo (JP); Hiroshi Sugawara, Tokyo (JP); Masami Murayama, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 115 days.

(21) Appl. No.: 14/232,887

(22) PCT Filed: Jul. 10, 2012

(86) PCT No.: PCT/JP2012/067576
§ 371 (c)(1),
(2), (4) Date: Jan. 14, 2014

(87) PCT Pub. No.: WO2013/011870
PCT Pub. Date: Jan. 24, 2013

(65) Prior Publication Data
US 2014/0163264 A1    Jun. 12, 2014

(30) Foreign Application Priority Data
Jul. 15, 2011   (JP) ................................. 2011-156322

(51) Int. Cl.
| | | |
|---|---|---|
| *C07C 29/76* | (2006.01) | |
| *C07C 29/80* | (2006.01) | |
| *B01D 61/58* | (2006.01) | |
| *B01D 61/36* | (2006.01) | |
| *B01D 61/14* | (2006.01) | |

(52) U.S. Cl.
CPC ............... *B01D 61/58* (2013.01); *C07C 29/76* (2013.01); *C07C 29/80* (2013.01); *B01D 61/147* (2013.01); *B01D 61/362* (2013.01); *B01D 2311/04* (2013.01); *B01D 2311/06* (2013.01); *B01D 2311/2623* (2013.01); *B01D 2311/2669* (2013.01)

(58) Field of Classification Search
USPC .......................................................... 568/913
See application file for complete search history.

(56) References Cited

FOREIGN PATENT DOCUMENTS

| | | | |
|---|---|---|---|
| JP | 54-033279 | A | 3/1979 |
| JP | 06-069175 | A | 3/1994 |
| JP | 09-057069 | A | 3/1997 |
| JP | 11-057304 | A | 3/1999 |
| JP | 11-506431 | A | 6/1999 |
| JP | 11-276801 | A | 10/1999 |
| JP | 2003-535836 | A | 2/2003 |
| JP | 2005-263792 | A | 9/2005 |
| JP | 2006-175330 | A | 7/2006 |
| JP | 2009-057286 | A | 3/2009 |
| JP | 2011-513056 | A | 4/2011 |
| WO | 96/36412 | A1 | 11/1996 |
| WO | 01/94284 | A2 | 12/2001 |
| WO | 2009/109686 | A1 | 9/2009 |

OTHER PUBLICATIONS

Buragohain P.V. et al., Novel resin-based ultrapurification system for reprocessing IPA in the semiconductor industry, Ind. Eng. Chem. Res., 1996, 35, pp. 3149-3154.

*Primary Examiner* — Elvis O Price
(74) *Attorney, Agent, or Firm* — Knobbe Martens Olson & Bear LLP

(57) ABSTRACT

A method of purifying an alcohol, such as isopropyl alcohol, includes a first ion exchange step of performing ion exchange treatment on an alcohol-containing liquid; a step of performing dehydration treatment using a dehydration membrane on the liquid treated in the first ion exchange step; a distillation step of performing distillation on the dehydration-treated liquid; and a second ion exchange step of further performing ion exchange treatment on the liquid obtained in the distillation step to obtain a purified alcohol.

12 Claims, 5 Drawing Sheets

METHOD AND APPARATUS FOR PURIFYING ALCOHOL

CROSS-REFERENCE TO RELATED APPLICATIONS

This application is the U.S. National Phase under 35. U.S.C. §371 of International Application PCT/JP2012/067576, filed Jul. 10, 2012, which claims priority to Japanese Patent Application No. 2011-156322, filed Jul. 15, 2011. The disclosures of the above-described applications are hereby incorporated by reference in their entirety. The International Application was published under PCT Article 21(2) in a language other than English.

TECHNICAL FIELD

The present invention relates to a method and apparatus for purifying an alcohol, and particularly to a method and apparatus suitable for purifying and recycling a recovered alcohol.

BACKGROUND ART

Alcohols, such as methyl alcohol, ethyl alcohol, and isopropyl alcohol (IPA), are used in large amounts as cleaning agents, solvents and synthetic raw materials for the chemical industry. Particularly, in the manufacturing step of a semiconductor device, a large amount of IPA is used in applications such as washing and drying. For example, an IPA evaporation drying method for performing water removal after performing pure water washing on a semiconductor device is effective as the process of performing water removal. On the other hand, a problem of the IPA evaporation drying method is that IPA, which has high volatility and of which high purity is required, is used, and as a result, the manufacturing cost of the semiconductor device increases. Therefore, in terms of cost reduction and an improvement in environmental load, it is desired to recover and reuse waste IPA which has been used in the semiconductor device manufacturing process. The IPA discharged from the manufacturing process of a semiconductor device contains impurities derived from the manufacturing process, the materials, and the equipment. In order to recover and reuse the IPA, it is necessary to remove these impurities to a high degree and purify the IPA to the same level as that in a case when it is purchased from the market for use in a semiconductor device manufacturing process. Main examples of the components of the impurities include water, ionic impurities, metals, and fine particles.

In commercial IPA, grades are set according to its applications, for example, use in a semiconductor device manufacturing process, and a standard value for each impurity is determined for each grade.

As a method of purifying an alcohol that is contaminated and contains impurities, a distillation method is known. However, when an attempt is made to purify an alcohol to a predetermined purity using only the distillation method, large-scale distillation equipment is required, and the equipment cost and the installation area increase, and enormous energy is required, and therefore, the energy cost also increases, which is not preferable in terms of economy.

For each impurity that may be contained in an alcohol, methods of removing the impurities from an alcohol are proposed as shown below.

For example, as a method of efficiently removing water in an alcohol, JP 11-276801A (Patent Literature 1) shows a method of setting water concentration in an alcohol to a certain level or less using a pervaporation (PV) method, and then removing water by adsorption using an adsorbent, such as zeolite. JP 6-69175A (Patent Literature 2) shows that water is separated from an alcohol using an anion exchange membrane as a separation membrane in a vapor permeation (VP) method, and the alcohol is further purified by distillation.

In the pervaporation method, a separation membrane having an affinity for a component (for example, water) that is the target of separation treatment is used, a mixed liquid containing the target component is flowed on the supply side of the separation membrane, and the pressure is reduced or an inert gas is flowed on the permeation side of the separation membrane to perform separation by the difference in permeation rate between each components in the separation membrane. The mixed liquid containing the target component is, for example, an alcohol which contains water as an impurity. Separation in a case where the fluid in contact with the membrane is in a gas phase is particularly referred to as the vapor permeation method. Separation in a case where the contact fluid is a liquid is referred to as the pervaporation method. In Patent Literature 1, as the separation membrane, a polyimide-based separation membrane or a cellulose-based separation membrane is used. In addition, as separation membranes for the dehydration of alcohols, zeolite membranes are also widely used. Zolite membranes are characterized in that: they have extremely strong water absorbency; regarding the adsorption of polar molecules, such as water molecules, they have high separation performance even when the partial pressure of the molecular species is extremely low; and the loss of the alcohol, the intended material, is small.

As methods of removing ionic impurities from an alcohol, methods using ion exchange resins are known as shown in JP 2009-57286A (Patent Literature 3), and Partha V. Buragohain, William N. Gill, and Steven M. Cramer; "Novel Resin-Based Ultrapurification System for Reprocessing IPA in the Semiconductor Industry," Ind. Eng. Chem. Res., 1996, 35(9), pp. 3149-3154 (Non-patent Literature 1). Treatment by an ion exchange resin is characterized in that: the energy and the equipment cost are smaller and the treatment is simpler than those in a case where a distillation apparatus is used; and an alcohol having high purity can be obtained. In the method using an ion exchange resin, an alcohol-containing liquid is passed through an ion exchange resin layer. In addition, JP 2005-263729A (Patent Literature 4) proposes a method of removing cationic impurities, such as metal ions, and fine particles by using an ion exchange membrane instead of an ion exchange resin layer and combining a filter and the ion exchange membrane.

JP 9-57069A (Patent Literature 5) discloses that distillation is further performed on an alcohol from which water has been removed by the pervaporation method, to remove metals, and the alcohol is then passed through a microfiltration membrane to remove insoluble fine particles.

JP 2003-112060A (Patent Literature 6) discloses a regeneration system adapted to combine various methods as described above, purify IPA recovered from a semiconductor device manufacturing process, and supply it to the semiconductor device manufacturing process again. Patent Literature 6 also discloses a purification method in such a regeneration system. In the system described in Patent Literature 6, a plurality of water removal units are provided, and water removal is repeatedly performed so that the content of water in a waste chemical reaches the raw material level of the chemical.

CITATION LIST

Patent Literature(s)

Patent Literature 1: JP 11-276801A
Patent Literature 2: JP 6-69175A

Patent Literature 3: JP 2009-57286A
Patent Literature 4: JP 2005-263729A
Patent Literature 5: JP 9-57069A
Patent Literature 6: JP 11-57304A
Patent Literature 7: JP 2003-112060A Non-Patent Literature(s)

Non-patent Literature 1: Partha V. Buragohain, William N. Gill, and Steven M. Cramer; "Novel Resin-Based Ultrapurification System for Reprocessing IPA in the Semiconductor Industry," Ind. Eng. Chem. Res., 1996, 35(9), pp. 3149-3154

SUMMARY OF INVENTION

Technical Problem

As described above, various methods are known as methods of purifying alcohols, such as IPA. Among these, in the method combining a pervaporation membrane and an adsorbent as shown in Patent Literature 1, water in the alcohol can be decreased, but the amount of energy consumption associated with the regeneration of the adsorbent is very large, which leads to an increase in cost, and a load may be applied on a distillation apparatus at the subsequent stage by an eluted material from the adsorbent. In the method combining vapor permeation by an anion exchange membrane and distillation as shown in Patent Literature 2, the separation factor of water with respect to IPA is about 160, which is very low compared with about 1000 that is the separation factor when a zeolite membrane is used, and the dehydration efficiency is poor, and therefore, the scale of the apparatus increases. In the method combining a filter and an ion exchange membrane as shown in Patent Literature 4, water and anionic impurities cannot be removed by this method alone. In addition, in the IPA regeneration system and purification method as shown in Patent Literature 6, ionic impurities eluted from a dehydration membrane in treatment by the dehydration membrane cannot be removed. In this manner, problems to be solved remain in the conventional methods of purifying alcohols.

It is an object of the present invention to provide a method and apparatus that can purify an alcohol typified by IPA with high purity.

Solution to Problem

The alcohol purification method according to the present invention includes: a first ion exchange step of performing ion exchange treatment on an alcohol-containing liquid; a step of performing dehydration treatment using a dehydration membrane on the liquid treated in the first ion exchange step; a distillation step of performing distillation on the dehydration-treated liquid; and a second ion exchange step of further performing ion exchange treatment on the liquid obtained in the distillation step to obtain a purified alcohol.

The alcohol purification apparatus according to the present invention includes: first ion exchange means for performing ion exchange treatment on an alcohol-containing liquid; a dehydration membrane that dehydrates the liquid treated by the first ion exchange means, by pervaporation or vapor permeation; distillation means for distilling the liquid dehydrated by the dehydration membrane; and second ion exchange means for further performing ion exchange treatment on the liquid obtained by the distillation means to obtain a purified alcohol.

According to the present invention, by combining first ion exchange treatment, membrane dehydration, distillation and second ion exchange treatment, impurities, such as water, ionic impurities, metals and fine particles, in an alcohol-containing liquid, can be removed to make low concentrations, and a purified alcohol having high purity can be obtained.

DESCRIPTION OF EMBODIMENTS

Figure 1:
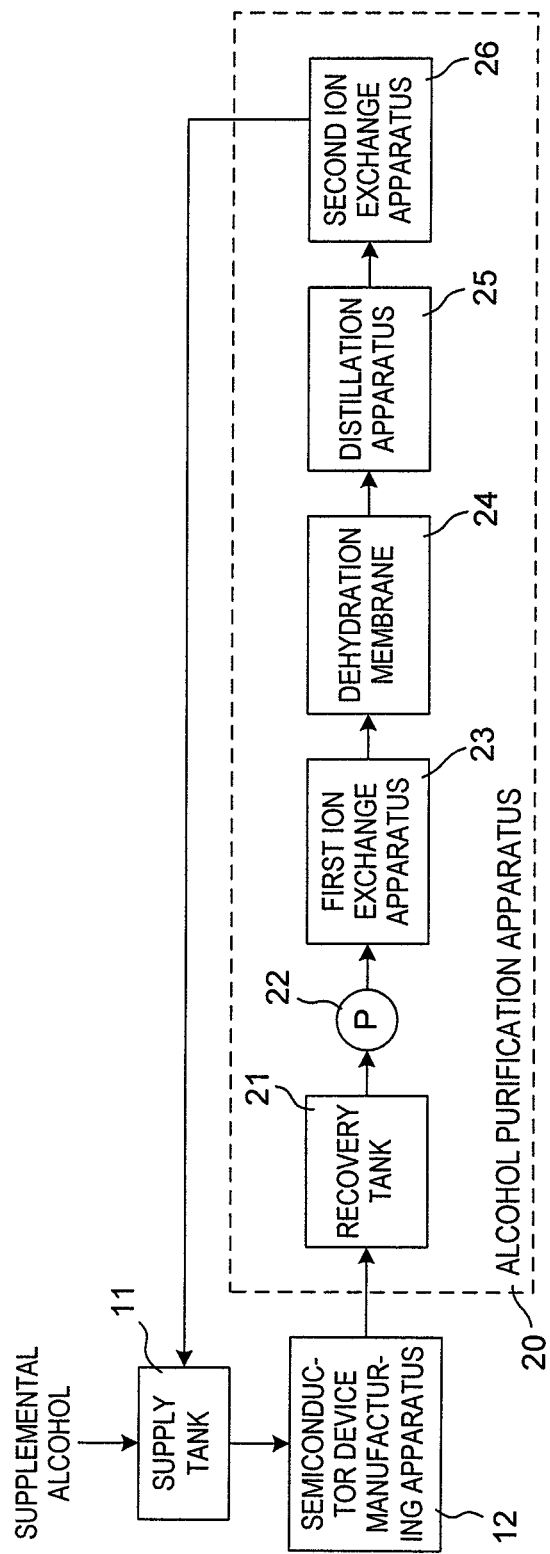
FIG. 1 is a diagram showing the configuration of an alcohol purification apparatus according to a first embodiment of the present invention.

Alcohol purification apparatus 20 according to the first embodiment of the present invention shown in FIG. 1 is preferably used for recovering and purifying an alcohol that is discharged from, for example, various processes such as a semiconductor device manufacturing process and contains impurities. In the example shown in FIG. 1, the alcohol to be purified is IPA (isopropyl alcohol). IPA that has been used in semiconductor device manufacturing apparatus 12 to contain impurities is recovered, and alcohol purification apparatus 20 purifies the recovered IPA, and supplies the purified IPA to semiconductor device manufacturing apparatus 12 again via supply tank 11. Supply tank 11 is adapted so that a supplementary alcohol is supplied to it in order to make up for a portion that is required at the start of operation or runs short during operation.

In alcohol purification apparatus 20, recovery tank 21 that temporarily holds the IPA recovered from semiconductor device manufacturing apparatus 12, as an alcohol-containing liquid, and pump 22 that is provided at the outlet of recovery tank 21 and feeds the alcohol-containing liquid are provided, and first ion exchange apparatus 23, dehydration membrane 24, distillation apparatus 25, and second ion exchange apparatus 26 are connected in series in this order to the outlet of this pump 22. The purified alcohol is obtained from the outlet of second ion exchange apparatus 26, and this purified alcohol is returned to supply tank 11 via piping.

Main examples of targets to be removed from the IPA in recovery tank 21 in alcohol purification apparatus 20 include water, ion components, which are cations and anions, fine particles, and so on.

First ion exchange apparatus 23 performs ion exchange treatment on the alcohol-containing liquid flowing in from pump 22, as first ion exchange means, and removes ion components in the alcohol-containing liquid using an ion exchange resin. By the ion exchange treatment by first ion exchange apparatus 23, the loads on distillation apparatus 25 and second ion exchange apparatus 26 at subsequent stages can be significantly decreased, and ion loads, such as acids and ionic metals, which are factors that deteriorate dehydration membrane 24 at the subsequent stage, can be decreased to promote longer life of dehydration membrane 24. First ion exchange apparatus 23 is arranged so that, for example, an ion exchange resin is packed in a tower-like container, and the liquid passes through the layer of the ion exchange resin. The cation exchange resin of the ion exchange resin removes cations, such as Na ions and Ca ions, and the anion exchange resin removes anions, such as Cl ions and acid components. The specifications of the cation exchange resin and the anion exchange resin packed in first ion exchange apparatus 23, and the apparatus configuration are determined according to the properties of the IPA supplied to first ion exchange apparatus 23 as the alcohol-containing liquid, and the quality required of the purified alcohol delivered from this alcohol purification apparatus 20. In terms of adsorption performance and low elution, an H (hydrogen ion) type strong acid cation exchange resin (SACER) and an OH (hydroxide ion) type strong base anion exchange resin (SBAER) are desirably used as the cation exchange resin and the anion exchange resin, respectively.

The ion exchange resin used in first ion exchange apparatus 23 may be any of the cation exchange resin or the anion exchange resin provided in a single bed, the cation exchange resin and the anion exchange resin provided in a double bed, or the cation exchange resin and the anion exchange resin provided in a mixed bed. In order to decrease ion loads, such as acids and ionic metals, which are factors that deteriorate dehydration membrane 24 at the subsequent stage, a mixed bed is preferable. When it is required that the water concentration in the final purified alcohol is decreased, or when it is desired that water elution from the ion exchange resin is decreased immediately after replace of the ion exchange resin in the ion exchange apparatus, a dry resin containing water as little as possible is preferably used as the ion exchange resin. For example, 15JS-HG•DRY, which is a dry, strong acid cation exchange resin and contains 2% or less of water, and MSPS2-1•DRY, which is a mixed-bed resin of a dry, strong acid cation exchange resin and a dry, weak base anion exchange resin and contains 10% or less of water, manufactured by ORGANO CORPORATION, and the like can be used.

Dehydration membrane 24 performs membrane dehydration by pervaporation (PV) or vapor permeation (VP) on the liquid treated by first ion exchange apparatus 23 to concentrate the alcohol. Dehydration membrane 24 is formed, for example, as a water-permeable membrane module. As the membrane, one composed of a polymer-based material, such as a polyimide-based, cellulose-based or polyvinyl alcohol-based material, or an inorganic material, such as zeolite, can be used. In terms of mechanical strength, dehydration performance, heat resistance and the like, a membrane containing zeolite as a material is preferably used as dehydration membrane 24.

Dehydration membrane 24 is generally operated at high temperature and under high pressure, and therefore, impurities may be eluted from the membrane material. In addition, for the ion exchange resin used in first ion exchange apparatus 23, it is difficult to effectively remove fine particles generated in semiconductor device manufacturing apparatus 12, and it is also difficult to remove ions of silica (silicon oxide) and the like, which have very low selectivity for the cation exchange resin or the anion exchange resin, over a long period. Therefore, distillation apparatus 25 as distillation means is provided at the stage subsequent to dehydration membrane 24, to perform a distillation operation on the liquid dehydrated by dehydration membrane 24. This distillation operation is not aimed at separating the alcohol and water by distillation, but at separating fine particles, salts, silica and metallic impurities from the alcohol.

Distillation apparatus 25 is, for example, a single-stage distillation apparatus. The impurities are concentrated in the distillation apparatus and the like by the distillation operation. In order to prevent some of these concentrated impurities from flowing out to the subsequent stage, means, for example, a drain valve, that periodically or steadily discharges some of the liquid in which the impurities are concentrated to the outside is preferably provided in distillation apparatus 25.

It is possible to remove impurities composed of salts and metal ions, and further impurities composed of fine particles by the distillation operation. However, these impurities remain accumulated in distillation apparatus 25 unless discharged, and therefore, when the impurities are concentrated, the impurities flow out to the subsequent stage by entrainment. It is possible to prevent some of the impurities from flowing out to the subsequent stage from distillation apparatus 25 by discharging some of the concentrated liquid out of the system. However, when the discharge amount to outside the system increases, the recovery rate of the alcohol decreases. In addition, when the concentration rate is constant in distillation and the concentration of the influent impurities increases, the concentration of the impurities on the concentrated side increases, and therefore, the concentration of the impurities discharged to the subsequent stage by entrainment ends up increasing. Further, it is also necessary to remove impurities eluted from stainless steel (SUS) piping generally used as a liquid feed line.

Therefore, in second ion exchange apparatus 26 as second ion exchange means, ion exchange treatment is further performed on the liquid obtained in distillation apparatus 25 to further lower the concentration of the ion components in the liquid discharged from distillation apparatus 25 to improve the purity of the alcohol. As second ion exchange apparatus 26, a tower-like container in which an ion exchange resin is packed, and an ion adsorption membrane can be used. When an ion exchange resin is used in second ion exchange apparatus 26, an ion exchange resin similar to that used in first ion exchange apparatus 23 can be used.

An ion adsorption membrane has a porous membrane material and has an ion exchange function. Such an ion adsorption membrane should be, for example, one having a pore diameter of 100 μm or less and having an ion exchange function, and its material, type and the like are not particularly limited. For example, a membrane material, such as a microfiltration membrane, into the surface of which a functional group having ion exchange ability is introduced can be used. Examples of the shape of the membrane material include a pleated type, a flat membrane type, a hollow fiber type and a porous body. An example of an ion adsorption membrane composed of a porous body is described in JP 2003-112060A (Patent Literature 7). As the ion exchange group introduced into the membrane material, any of a cation exchange group, a chelate exchange group and an anion exchange group, or a combination of at least two of these according to the eluted components can be used. The present inventors discovered that, compared with an ion exchange resin, an ion adsorption membrane can rapidly replace water in the matrix by an alcohol until the intended water concentration is reached, and is also excellent in the reaction rate of ion exchange. Therefore, by using an ion adsorption membrane as second ion exchange apparatus 26, treatment at a higher flow rate is possible without increasing water concentration. In addition, the ion adsorption membrane has porosity, and therefore, it is also possible to remove some fine particles.

Figure 2:
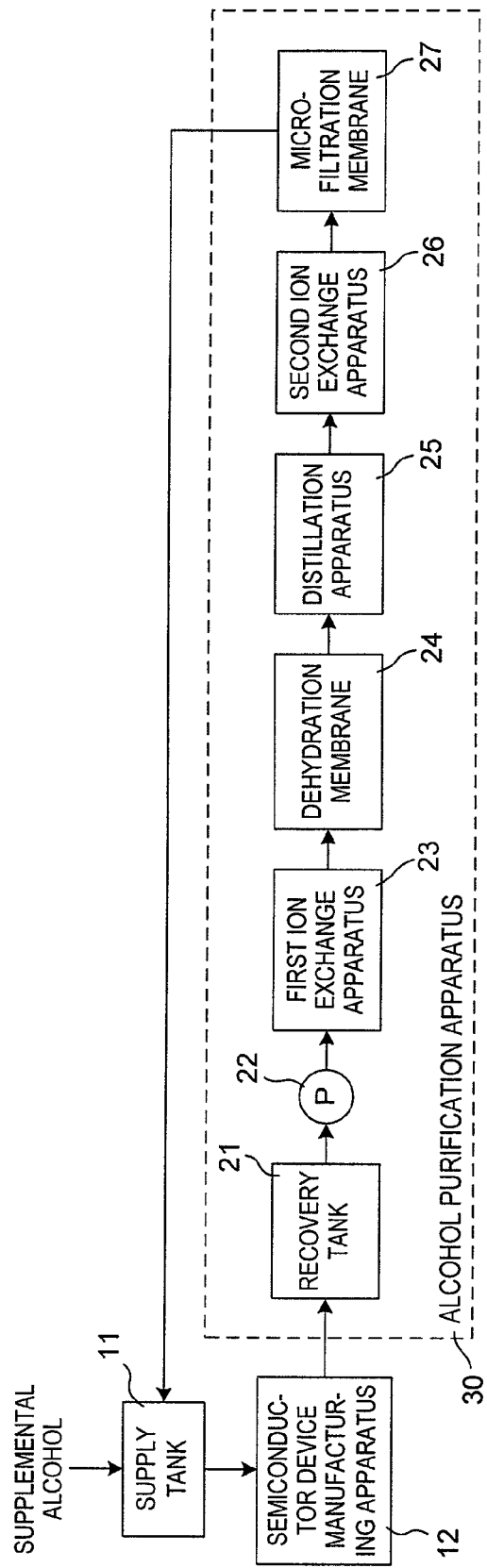
FIG. 2 is a diagram showing the configuration of an alcohol purification apparatus according to a second embodiment of the present invention.

FIG. 2 shows an alcohol purification apparatus according to the second embodiment of the present invention. Alcohol purification apparatus 30 shown in FIG. 2 is obtained by providing microfiltration membrane 27 at the stage subsequent to second ion exchange apparatus 26 in alcohol purification apparatus 20 shown in FIG. 1. The present inventors discovered that when iron (Fe) and aluminum (Al) are present in an alcohol liquid as impurities, these iron and aluminum impurity components tend to easily become colloidal under the condition of low water concentration, for example, the condition of a water concentration of 1000 ppm or less, and that it is difficult to remove these impurity components by an ion adsorption membrane, but, on the other hand, it is possible to remove these impurity components using a microfiltration membrane having a pore diameter of 20 nm or less.

When fine particles are also present in the alcohol liquid in addition to the colloidal iron and aluminum impurities, a microfiltration membrane which is used for the removal of fine particles and has a pore diameter of 50 nm or more is preferably provided at the stage prior to the microfiltration membrane having a pore diameter of 20 nm or less.

Figure 3:
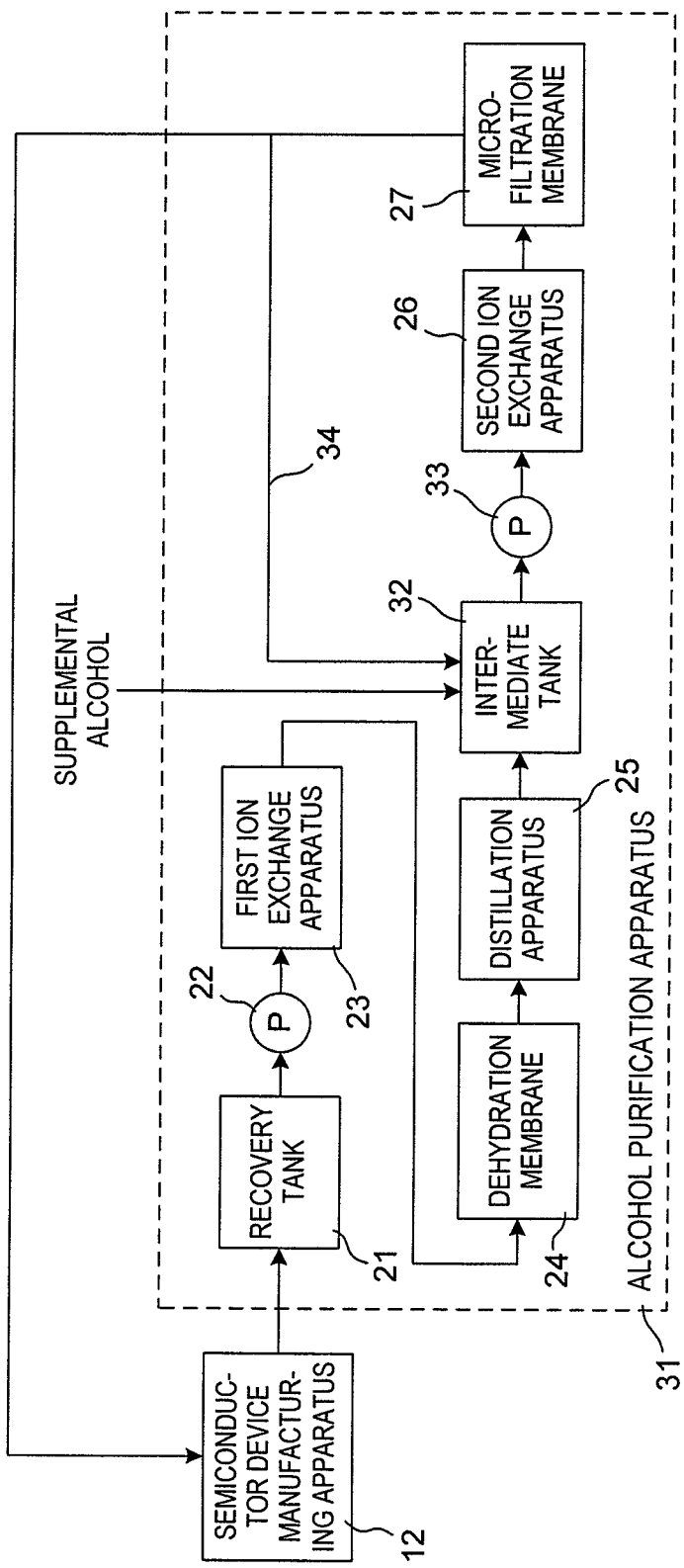
FIG. 3 is a diagram showing the configuration of an alcohol purification apparatus according to a third embodiment of the present invention.

FIG. 3 shows an alcohol purification apparatus according to the third embodiment of the present invention. Alcohol purification apparatus 31 shown in FIG. 3 is obtained by providing intermediate tank 32 temporarily storing an alcohol liquid and pump 33 feeding the alcohol liquid from intermediate tank 32, at the stage prior to second ion exchange apparatus 26 in alcohol purification apparatus 30 shown in FIG. 2. No supply tank is provided at the stage prior to semiconductor device manufacturing apparatus 12. Second ion exchange apparatus 26 and microfiltration membrane 27 are connected in series in this order to the outlet of pump 33, and the purified alcohol is obtained from the outlet of microfiltration membrane 27. In order to accommodate fluctuations in the amount of the alcohol used in semiconductor device manufacturing apparatus 12, pump 33 is adapted to be able to circulate a constant amount of the alcohol liquid, and the outlet of microfiltration membrane 27 is connected to semiconductor device manufacturing apparatus 12, and also connected to intermediate tank 32 via branch piping 34. Branch piping 34 is used to return the purified alcohol obtained from microfiltration membrane 27 directly to intermediate tank 32. By these, the total amount or some of the purified alcohol obtained from microfiltration membrane 27 is supplied to semiconductor device manufacturing apparatus 12, and the remaining amount is returned to intermediate tank 32. Therefore, a circulation system for the purified alcohol is composed of intermediate tank 32, pump 33, second ion exchange apparatus 26, microfiltration membrane 27 and branch piping 34. In addition to the alcohol liquid from distillation apparatus 25 and the purified alcohol from microfiltration membrane 27, a supplementary alcohol is supplied to intermediate tank 32 in order to make up for a portion that is required at the start of operation or runs short during operation.

In alcohol purification apparatus 31 shown in FIG. 3, the purified alcohol circulates in the above-described circulation system even when the supply of the alcohol is not required on the semiconductor device manufacturing apparatus 12 side, and residence of the alcohol in the tank, the piping and the like can be prevented. Therefore, there are no eluted impurities, and a high purity alcohol can always be supplied.

EXAMPLES

The present invention will be described in detail below based on Examples. However, the present invention is not limited by the following Examples.

Example 1

Among the configuration shown in FIG. 2, the portion corresponding to alcohol purification apparatus 30 was assembled. As first ion exchange apparatus 23, one packed with a gel type ion exchange resin ESG-2 manufactured by ORGANO CORPORATION, which was a mixed-bed ion exchange resin of a strong acid cation exchange resin and a strong base anion exchange resin, was used. The ion exchange resin was used in the state of containing water. As dehydration membrane 24, a membrane containing A-type zeolite as a material was used, and dehydration treatment by the vapor permeation method was performed. For second ion exchange apparatus 26, an ion adsorption membrane manufactured by Asahi Kasei Corporation was used, and as microfiltration membrane 27, one having a pore diameter of 0.02 μm was used.

An alcohol-containing liquid in which the water concentration in IPA was 5% was supplied to recovery tank 21, and passed through first ion exchange apparatus 23, dehydration membrane 24, distillation apparatus 25, second ion exchange apparatus 26 and microfiltration membrane 27 in this order by pump 22 at a liquid passage rate of 2 kg/hour. The water concentration and the concentration of metal components at the respective outlets of recovery tank 21, first ion exchange apparatus 23, dehydration membrane 24, distillation apparatus 25, second ion exchange apparatus 26 and microfiltration membrane 27 were measured. For the measurement of the water concentration, a Karl Fischer water concentration meter (manufactured by Hiranuma Sangyo Co., Ltd.) was used, and for the measurement of the concentration of metal components, ICP-MS (inductively coupled plasma-mass spectrometer) was used. The analytical lower limit value of each metal ion in the metal component concentration measurement was 0.05 ppb. The results of the water concentration measurement are shown in FIG. 4, and the results of the metal component concentration measurement are shown in FIG. 5.

Figure 4:
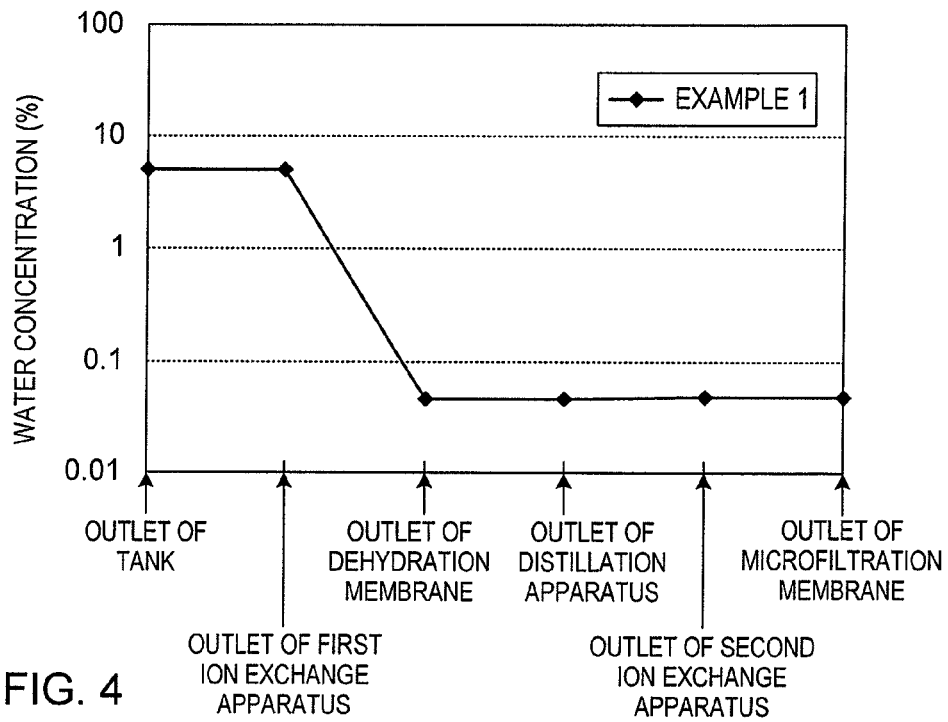
FIG. 4 is a graph showing water concentration at the outlet of each step in Example 1.
Figure 5:
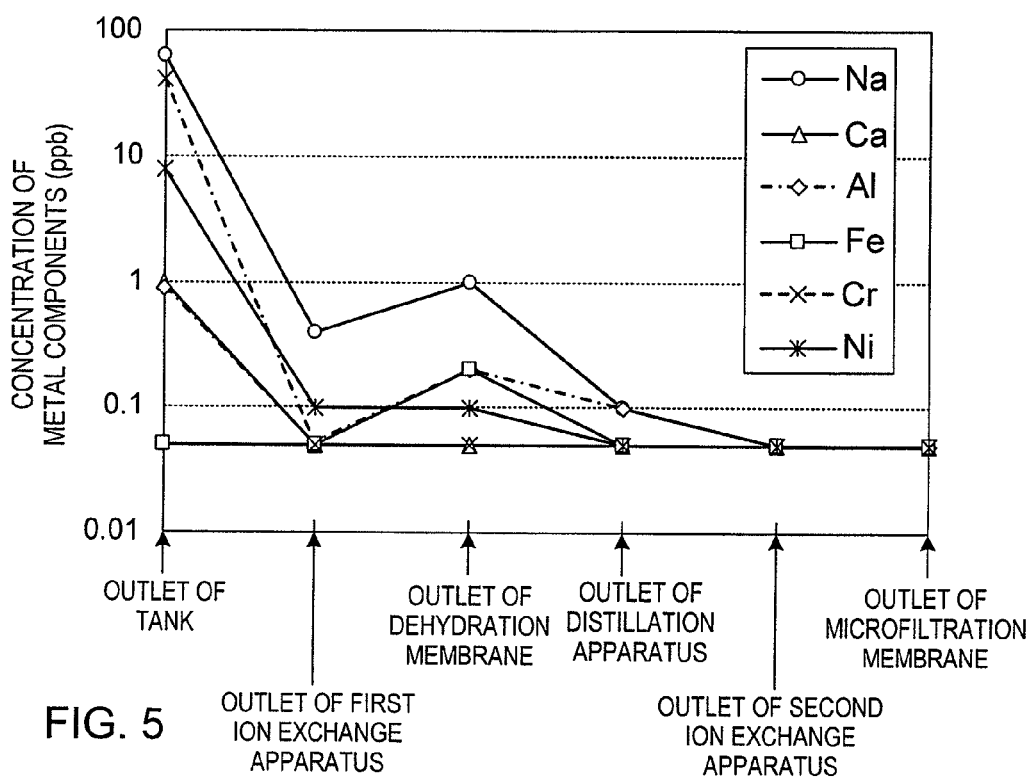
FIG. 5 is a graph showing the concentration of each metal component at the outlet of each step in EXAMPLE 1.

As seen from FIG. 4, the water concentration in the liquid became stable at and after dehydration membrane 24, and the water concentration at the outlet of microfiltration membrane 27 was 0.046%. Regarding the concentration of metal components shown in FIG. 5, it was observed that the concentration of metal components decreased significantly by passing the liquid through first ion exchange apparatus 23, but at the outlet of dehydration membrane 24, due to the elution of metals considered to be from the constituent members, the concentration increased for some metals. At the outlet of evaporation apparatus 25, the concentration of metal components decreased again, but the outflow of some metals was seen. However, it was confirmed that at the outlet of second ion exchange apparatus 26, all metal components were removed until their concentration reached less than the analytical lower limit value.

In addition, silica concentration was measured under similar conditions. At both the outlets of recovery tank 21 and first ion exchange apparatus 23, the silica concentration was equal to or less than 0.2 ppb, which was the analytical lower limit, and at the outlet of dehydration membrane 24, due to elution considered to be from the constituent members, the silica concentration reached 1.8 ppb. On the other hand, at the outlet of distillation apparatus 25, the silica concentration was equal to or less than 0.2 ppb, which was the analytical lower limit value, and it was confirmed that silica was removed by distillation. In addition, also at the outlets of second ion exchange apparatus 26 and microfiltration membrane 27, the silica concentration was 0.2 ppb or less, and no increase in the elution of silica was observed.

Example 2

Figure 6:
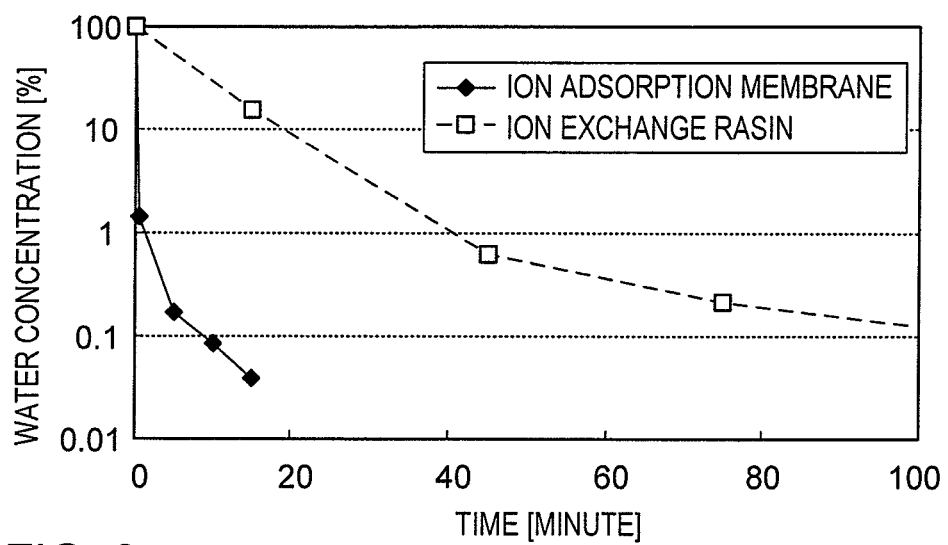
FIG. 6 is a graph showing temporal changes in the amount of water at the outlet of the ion exchange resin outlet and at the outlet of the ion adsorption membrane.

For each of an ion exchange resin and an ion adsorption membrane, the ease of alcohol replacement was studied. An ion adsorption membrane module (manufactured by Asahi Kasei Corporation) washed with ultrapure water, and a column packed with an ion exchange resin (manufactured by ORGANO CORPORATION) washed with ultrapure water were prepared. High purity IPA (manufactured by Tokuyama Corporation) was passed through each, and the water concentration of the liquid at the outlet of each was measured using a Karl Fischer water concentration meter (manufactured by Hiranuma Sangyo Co., Ltd.) until the water concentration reached 0.1% or less. The relationship between liquid passage time and the water concentration at the time is shown in FIG. 6. As shown in FIG. 6, in the ion adsorption membrane, the water concentration at the outlet reached 0.1% or less within 20 minutes from the start of liquid passage, whereas, in the ion exchange resin, the water concentration at the outlet was 0.1% or more even after a lapse of 1 hour or more from the start of liquid passage. From these results, it is found that, compared with the ion exchange resin, the ion adsorption membrane can rapidly replace contained water by the alcohol. Therefore, it is found that it is more preferable to use an ion adsorption membrane than an ion exchange resin for second ion exchange apparatus 25 provided at the stage subsequent to dehydration membrane 24.

Example 3

Next, it is shown that in order to decrease iron and aluminum as impurities to infinitesimal amounts when the water concentration in an alcohol is low, treatment by a microfiltration membrane should be performed at the stage subsequent to treatment by an ion adsorption membrane.

IPA in which the amount of water was 1000 ppm, and each content of Fe and Al was adjusted to 10 ppb was passed through an ion adsorption membrane (manufactured by Asahi Kasei Corporation) which had a cation exchange group, and then passed through a microfiltration membrane (manufactured by Nihon Entegris K.K.) which had a pore diameter of 20 nm and had a matrix made of polyethylene. The concentration of the metal components of the liquid at outlet of the ion adsorption membrane and the outlet of the microfiltration membrane are shown in TABLE 1. From the results, it is found that Fe and Al that were not removed by the ion adsorption membrane and flowed out were removed in the microfiltration membrane.

TABLE 1

| | Al concentration (ppb) | Fe concentration (ppb) |
|---|---|---|
| Inlet of ion adsorption membrane | 10 | 10 |
| Outlet of ion adsorption membrane | 6 | 6 |
| Outlet of microfiltration membrane | <0.05 | <0.05 |

Comparative Example 1

An experiment similar to that of EXAMPLE 3 was performed except that the amount of water was 4000 ppm. The results are shown in TABLE 2. From this, it is found that unless the amount of water in IPA is 0.1% or less, Fe and Al cannot be removed by the microfiltration membrane.

TABLE 2

| | Al concentration (ppb) | Fe concentration (ppb) |
|---|---|---|
| Inlet of ion adsorption membrane | 10 | 10 |
| Outlet of ion adsorption membrane | 6 | 6 |
| Outlet of microfiltration membrane | 5 | 5 |

Comparative Example 2

An experiment similar to that of EXAMPLE 3 was performed except that a microfiltration membrane (manufactured by Nihon Entegris K.K.) which had a pore diameter of 30 nm was used. The results are shown in TABLE 3. From this, it is found that unless the pore diameter of the microfiltration membrane is 20 nm or less, Fe and Al cannot be removed to make low concentration by the microfiltration membrane.

TABLE 3

| | Al concentration (ppb) | Fe concentration (ppb) |
|---|---|---|
| Inlet of ion adsorption membrane | 10 | 10 |
| Outlet of ion adsorption membrane | 6 | 6 |
| Outlet of microfiltration membrane | 2 | 1 |

REFERENCE SIGNS LIST 11 supply tank;
12 semiconductor device manufacturing apparatus;
20, 30, 31 alcohol purification apparatus;
21 recovery tank;
22, 33 pump;
23 first ion exchange apparatus;
24 dehydration membrane;
25 distillation apparatus;
26 second ion exchange apparatus;
27 microfiltration membrane;
32 intermediate tank;
34 branch piping.

What is claimed is:

1. An alcohol purification method comprising:
   a first ion exchange step of performing ion exchange treatment on an alcohol-containing liquid;
   a step of performing dehydration treatment using a dehydration membrane on a liquid treated in said first ion exchange step;
   a distillation step of performing distillation on the dehydration-treated liquid; and
   a second ion exchange step of further performing ion exchange treatment on a liquid obtained in said distillation step to obtain a purified alcohol.

2. The alcohol purification method according to claim 1, wherein said second ion exchange step is a step of passing a liquid through an ion adsorption membrane.

3. The alcohol purification method according to claim 1, further comprising a filtration step of performing filtration treatment using a microfiltration membrane on a liquid obtained in said second ion exchange step.

4. The alcohol purification method according to claim 1, wherein the dehydration membrane containing zeolite as a material is used.

5. An alcohol purification apparatus comprising:
   first ion exchange means for performing ion exchange treatment on an alcohol-containing liquid;
   a dehydration membrane that dehydrates a liquid treated by said first ion exchange means, by pervaporation or vapor permeation;
   distillation means for performing a liquid dehydrated by said dehydration membrane; and
   second ion exchange means for further performing ion exchange treatment on a liquid obtained by said distillation means to obtain a purified alcohol.

6. The alcohol purification apparatus according to claim 5, wherein said second ion exchange means comprises an ion adsorption membrane.

7. The alcohol purification apparatus according to claim 5, further comprising a microfiltration membrane at a stage subsequent to said second ion exchange means.

8. The alcohol purification apparatus according to claim 5, wherein said dehydration membrane contains zeolite as a material.

9. The alcohol purification method according to claim 2, further comprising a filtration step of performing filtration treatment using a microfiltration membrane on a liquid obtained in said second ion exchange step.

10. The alcohol purification method according to claim 2, wherein the dehydration membrane containing zeolite as a material is used.

11. The alcohol purification apparatus according to claim 6, further comprising a microfiltration membrane at a stage subsequent to said second ion exchange means.

12. The alcohol purification apparatus according to claim 6, wherein said dehydration membrane contains zeolite as a material.

* * * * *